United States Patent
Driesen et al.

(10) Patent No.: US 6,957,468 B2
(45) Date of Patent: *Oct. 25, 2005

(54) TOOTHBRUSH HEAD WITH ANCHOR-FREE BRISTLE TUFTING

(75) Inventors: Georges Driesen, Weilrod (DE); Thomas Fritsch, Eppstein (DE)

(73) Assignee: Braun GmbH, Kronberg (DE)

( * ) Notice: Subject to any disclaimer, the term of this patent is extended or adjusted under 35 U.S.C. 154(b) by 120 days.

This patent is subject to a terminal disclaimer.

(21) Appl. No.: 10/142,224

(22) Filed: May 9, 2002

(65) Prior Publication Data

US 2002/0166188 A1 Nov. 14, 2002

(30) Foreign Application Priority Data

May 12, 2001 (DE) .......................................... 101 23 258

(51) Int. Cl.[7] .............................. A46B 9/04; A46B 7/08; A46B 9/08; A46B 3/00
(52) U.S. Cl. ........................ 15/167.1; 15/183; 15/190; 15/199; 15/191.1; 15/192; 15/193; 300/21
(58) Field of Search ............................... 15/180, 167.1, 15/191.1, 192, 193, 195, 199, 204, 205, 183, 198; 300/21

(56) References Cited

U.S. PATENT DOCUMENTS

| | | | |
|---|---|---|---|
| 1,191,556 A | 7/1916 | Blake | |
| 2,982,983 A | * 5/1961 | Peterson | ...................... 15/180 |
| 3,139,094 A | 6/1964 | Efeian | |
| 4,892,698 A | 1/1990 | Weihrauch | |
| 4,988,146 A | 1/1991 | Weihrauch | |
| 5,045,267 A | 9/1991 | Weihrauch | |
| 5,224,763 A | 7/1993 | Dirksing | |
| 5,318,352 A | 6/1994 | Holland | |
| 5,446,940 A | 9/1995 | Curtis et al. | |
| 5,590,438 A | 1/1997 | Chen et al. | |
| 5,687,446 A | 11/1997 | Chen et al. | |
| 5,823,633 A | 10/1998 | Weihrauch | |
| 5,850,660 A | 12/1998 | O'Halloran | |
| 5,967,617 A | * 10/1999 | Zapanta | ....................... 300/21 |
| 6,009,589 A | 1/2000 | Driesen et al. | |
| 6,021,538 A | 2/2000 | Kressner et al. | |
| 6,035,476 A | 3/2000 | Underwood et al. | |
| 6,260,928 B1 | * 7/2001 | Collins et al. | ................. 300/21 |
| 6,457,202 B1 | * 10/2002 | Torres et al. | ................. 15/180 |
| 6,665,901 B2 | * 12/2003 | Driesen et al. | ............. 15/167.1 |
| 6,786,558 B2 | * 9/2004 | Driesen et al. | ............... 300/21 |
| 2001/0023516 A1 | 9/2001 | Driesen et al. | |

FOREIGN PATENT DOCUMENTS

| | | |
|---|---|---|
| CA | 2327493 | 11/1999 |
| DE | 36 24 343 | 5/1988 |
| DE | 91 14 362.4 | 1/1992 |
| DE | 42 14 903 | 5/1994 |
| DE | 42 24 903 | 3/1996 |
| DE | 195 19 291 | 11/1996 |
| DE | 195 45 030 | 6/1997 |
| EP | 0 700 259 | 3/1996 |
| EP | 0 679 368 | 8/1999 |
| EP | 0 972 464 | 1/2000 |
| WO | WO 97/03587 | 2/1997 |

* cited by examiner

Primary Examiner—John Kim
Assistant Examiner—Shay L. Balsis
(74) Attorney, Agent, or Firm—Fish & Richardson P.C.

(57) ABSTRACT

The invention is directed to a brush head, in particular a toothbrush head, having a bristle carrier and bristles attached thereto, which are seated in the form of tufts in holes in the bristle carrier and fastened by their ends close to the bristle carrier to the bristle carrier without anchoring, in particular by welding and/or adhesive bonding to a rear side of the bristle carrier using the method referred to as anchor-free tufting. According to the invention, at least one hole (2) in the bristle carrier (1) is divided by means of at least one transverse wall (4) into several segments and said at least one transverse wall is constructed such that the bristles seated in the segments form a common tuft (3) with a smooth and closed outer contour corresponding to the contour of the hole and are supported by the transverse wall.

27 Claims, 4 Drawing Sheets

TOOTHBRUSH HEAD WITH ANCHOR-FREE BRISTLE TUFTING

TECHNICAL FIELD

This invention relates to a brush head, in particular a toothbrush head, having a bristle carrier and bristles attached thereto, which are seated in the form of tufts in holes in the bristle carrier and fastened by their ends close to the bristle carrier to the bristle carrier without anchoring, in particular by welding and/or adhesive bonding to a rear side of the bristle carrier.

BACKGROUND

Unlike the method referred to as anchor tufting which includes arranging the tufts in a U-shaped configuration and, with the aid of small metal anchor plates placed between the legs of the U-shaped tufts, inserting them into a blind-end bore in the bristle carrier where they are fastened by shooting the anchor plate into opposite side walls of the blind-end bore, the bristles are not arranged in U shape in the anchor-free tufting method. In the method referred to as anchor-free tufting the bristles are seated with their one ends in the holes in the bristle carrier while the opposite ends project out freely, forming the working ends of the bristles. The ends seated in the holes are fastened, for example, by welding or adhesive bonding to the bristle carrier.

From DE 195 45 030A1 there is known a brush with inserted tufts fastened by means of anchor plates. Perforating dies, with which it is possible to form holes of a cross section exceeding that of a single tuft, are provided to form at least a part of the tuft holes in the bristle carrier. Toward their one end these perforating dies have indentations that are open at the edge to create an intermediate bar or a partition wall within the complete hole cross section. Hence the complete hole is formed of hole sub-sections with a cross section corresponding in each case to approximately the cross section of the tuft. It is thus possible to manufacture brushes with bristle sub-fields made up of several individual tufts. The intermediate bars or partition walls are comprised of the same material as the bristle carrier itself, which is generally plastic. To fasten the tufts with the anchor plates it is however necessary for these plastic partition walls to be of sufficient thickness so as not to bend during the tufting operation. Consequently, a relatively wide gap remains between the individual tufts inserted in the hole subsections with the result that, on the one hand, the tufts located in the complete hole cross section do not form a homogeneous field of bristles and, on the other hand, the stability of the individual bristles is reduced because they are no longer able to lend each other mutual support on account of the presence of the relatively thick plastic partition walls and the attendant gap formation.

A toothbrush with tufts fastened by the anchor-free tufting method is presented in WO 99/55194 or EP 0972464A1, for example. Such brush heads with anchor-free fastened tufts are capable of improvement in several respects:

One problem concerns the service life of such brushes. Premature wear occurs as the result of a relatively severe movement of the bristles, particularly in the case of tufts with a non-circular outer contour. On account of the special fastening of the bristles the free and hence bendable length of the bristles at the one end of the bristles is bigger compared to tufts fastened by the anchor tufting method, with the result that otherwise identical bristles are easier to bend when secured by the anchor-free tufting method.

Movability also has an adverse effect on dental cleaning efficiency and reduces the subjectively perceived stiffness of the brush head. As a rule, higher cleaning forces are applied on account of the perceived softness of the brush head. Where electric toothbrushes are concerned, this can reduce the angle of oscillation of the brush head on account of play in the toothbrush gearing, thus impairing cleaning performance.

Room for improvement also exists with regard to appearance. With the anchor-free tufting method there is a risk of the bristles within a tuft being pushed over each other, making it impossible to perceive a clear-cut, colored border between color-segregated areas of tufts.

SUMMARY OF THE INVENTION

It is therefore an object of the present invention to provide an improved brush head of the type initially referred to, which eliminates the disadvantages of the prior art and advances it in advantageous manner. In particular it is intended to improve the anchor-free fastening of the tufts, thus eliminating the previously mentioned disadvantages.

According to the invention the brush head has at least one hole in the bristle carrier, which is divided by means of at least one transverse wall into several segments, the at least one transverse wall being constructed such that the bristles seated in the segments form a common tuft with a smooth and closed outer contour corresponding to the contour of the hole. In other words, seated in the hole is a tuft, which or whose fastening in the hole is divided into several segments but still outwardly forms a uniform tuft field. The transverse wall forms a support wall in the interior of the hole, upon which the bristles of a tuft can take support as well as on the peripheral wall of the hole, particularly to prevent bending. More specifically, this also provides support for those bristles that do not lie around the outer periphery of the hole, making the tuft in question stiffer on the whole. The transverse or support wall reduces the effectively available bending length of the bristles because they can no longer bend freely down to their ends seated in the hole, including the part received in the hole, but are again supported against bending at a point above their ends seated in the holes. The respective tuft thus acquires greater stiffness (the stiffness of a bristle being roughly proportional to its diameter to the power of four divided by the free length of the bristle to the power of three) and the movability of the bristles is reduced, with the result that the user of the brush perceives a greater stiffness of the brush head and cleans accordingly with less force. Bristle wear is reduced and the efficiency of the cleaning operation is improved because the previously described advantages no longer arise. In addition to this it is possible to create, for example, a clear-cut border between variously colored filaments of a tuft by dividing the hole into several segments.

A further important positive effect of the use of such support walls for tufts fastened to the bristle carrier by the anchor-free tufting method is that the tufts acquire comparable characteristics, in particular comparable stiffness, to those tufts fastened by the anchor tufting method, with the result that their clinical test results are also well comparable. Valuable findings can be drawn and applied from this, and the time and cost for developing the brushes and for conducting separate series of clinical tests can be saved.

In a further aspect of the invention provision is made for at least one transverse wall to divide holes of the bristle carrier that have an elongated outer contour in the manner of a slot, each accordingly receiving one tuft with a similarly elongated outer contour. The at least one transverse wall preferably extends in a direction approximately transverse to the longitudinal axis of the respective hole. It should be noted in this connection that the longitudinal axis of the hole does not need to be a straight line but can also be curved, as is the case in particular with round toothbrush heads of electric toothbrushes. It will be appreciated, of course, that the holes in which the transverse walls are arranged can also have other shapes. For example, said holes can also be rectangular, circular or essentially triangular, in which case the transverse walls are then arranged in the hole in star form, a meandering pattern or the like in order to divide the hole into sub-sections. In the case of arcuately curved elongate holes it is possible, for example, to provide one transverse wall extending along an arcuate central axis of the elongate hole, with one or several additional transverse walls arranged in a direction transverse to said transverse wall. The configuration and arrangement of the transverse walls in the hole depend on the geometry in question and can be of diverse nature. Particularly in the case of holes with a contour other than circular there are considerable advantages to be gained from the incorporated support walls because without them there would be severe movement and easy bending of the bristles due to the lack of support of the bristles in the direction of the longitudinal axis of the hole.

The thickness of the at least one transverse wall preferably amounts to just a fraction of a millimeter so as not to create a gap in the tuft. According to an advantageous embodiment of the invention the thickness of the transverse wall for standard tufts with a diameter of between 1.5 mm and 1.7 mm can lie in the range from 0.2 mm to 0.3 mm. If thicker tufts are used, the wall thickness can be reinforced accordingly.

In another feature of the invention the at least one transverse wall is recessed in the hole. An upper edge of the transverse wall is recessed relative to an upper side of the bristle carrier in which the holes are constructed.

The amount of recessing relative to the upper side of the bristle carrier can be variously selected. According to a preferred embodiment of the invention the difference in height between the upper edge of the at least one transverse wall and the upper side of the bristle carrier lies in the range from 0.1 mm to 0.7 mm, preferably around 0.25 mm to 0.5 mm. The support walls thus remain invisible and the tufts retain their full, uniform appearance.

To prevent a gap forming between the segments of a tuft added provision can be made for the at least one transverse wall to taper in thickness toward its upper side, in particular for it to be conically shaped. Opposing sides of the transverse wall are upwardly inclined in V-shape, with the result that the bristles converge, forming a closed, dense tuft without any gaps. Such a construction of the support or transverse wall also makes it easier to insert the bristles in the corresponding hole.

Provision can also be made for the upper edge of the transverse wall to be rounded off so that the bristles take a harmonious course on the one hand and bristle wear against the upper edge of the transverse wall is prevented on the other hand. Semi-elliptical cross sections and similarly rounded forms of the support wall are possible.

In a further aspect of the invention the at least one transverse wall is integrally constructed in one piece with the bristle carrier. In particular it can be injection-molded of plastic together with the bristle carrier.

To support the bristles a metal anchor plate constructed separately from the bristle carrier could also be subsequently inserted in the hole, in particular shot into position, for the sole purpose of supporting the bristles against bending, unlike its real purpose in the anchor tufting method, which is to fasten the bristles. It would also be possible to provide a wire-shaped cross bar or the like. However, the embodiment previously mentioned with the transverse wall integrally injection-molded in one piece with the bristle carrier obviates the need for a further separate assembly or production step.

The alignment of the at least one transverse wall in the hole in the bristle carrier can be adapted to the special configuration of the tuft or the hole. An advantageous embodiment is for the at least one transverse wall to be arranged perpendicular to the upper side of the bristle carrier. The bristles are thus aligned or supported to project in an essentially perpendicular direction.

According to a further preferred embodiment of the invention the at least one transverse wall can be arranged at an inclination. In particular it can be inclined at an acute angle to the bristle carrier normal, which stands perpendicular to the upper side of the bristle carrier.

The inclined arrangement of the transverse wall can be provided in particular for inclined tufts. The transverse wall preferably extends parallel to the tuft axis. The outer walls of the corresponding hole, which extend parallel to the inclined transverse wall, can also have a correspondingly inclined construction.

According to a further variant the at least one transverse wall can also be inclined in opposition to the tuft axis.

The arrangement of the transverse wall or walls with respect to the base area of the respective hole can be variously selected. Advantageously, the transverse walls are arranged such that the respective hole is divided into segments of roughly the same size. The various tuft segments thus take on approximately the same stiffness, with the result that a tuft with on the whole homogenous characteristics can be obtained.

The holes in the bristle carrier are preferably through-holes in the essentially disk-shaped or plate-shaped bristle carrier, which for an electric toothbrush can have the form of a plane disk. The bristles project with their one ends out of the holes at the rear side of the bristle carrier. Here they can be welded or joined together by adhesive bonding, for example by means of an embossing die, as is generally known in the art.

Different bristles can be seated in different segments of a hole in the bristle carrier. The joint tuft is built up accordingly of various bristles. Bristles of the same type are preferably seated within one segment.

In a further aspect of the invention the segments of the divided hole have a non-circular contour. In particular it is possible to provide segments with, for example, a roughly polygonal contour, which have at least two parallel sides. The transverse wall can have a straight construction, like the side walls of an elongated hole in the bristle carrier.

All the findings of the present application can similarly be applied or used for hand toothbrushes or motor-driven toothbrushes.

Further objects, advantages, features and application possibilities of the present invention will become apparent from the subsequent description of embodiments with reference to the accompanying drawings. In this context, all features described and/or depicted, whether individually or in any reasonable combination, constitute the object of this invention irrespective of their summary in the claims or the cross references of the latter.

DETAILED DESCRIPTION

Figure 1:
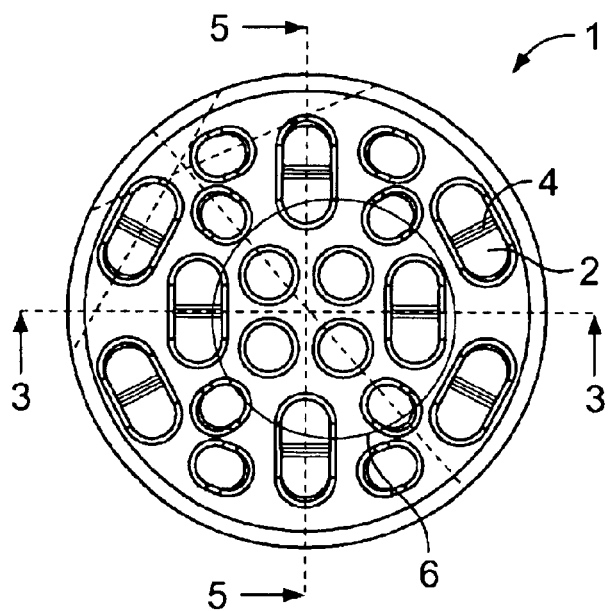
FIG. 1 is a top view of the upper side of a bristle carrier of a toothbrush head for an electric toothbrush.
Figure 2:
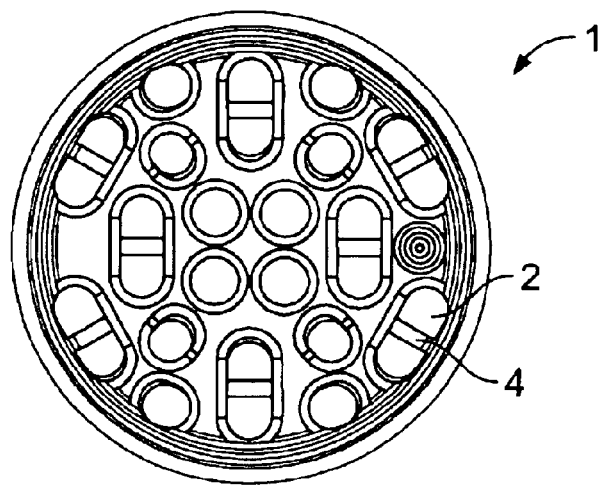
FIG. 2 is a top view of the underside of the bristle carrier of FIG. 1.
Figure 3:
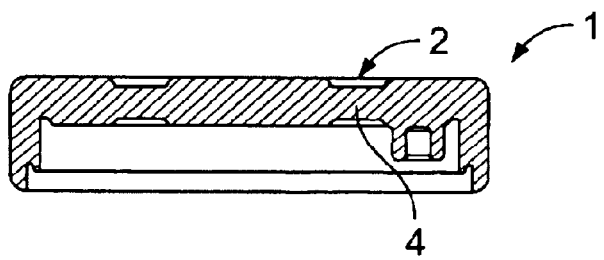
FIG. 3 is a sectional view of the bristle carrier of FIG. 1 taken along the line 3—3 of FIG. 1.

FIGS. 1 to 3 show the bristle carrier 1, which is essentially constructed as a plane disk with peripheral edges projecting downward which are designed to be secured to the bottom part of a toothbrush head of an electric toothbrush in a snap-fit arrangement or by welding in a manner known in the art. The bristle carrier 1 has a multiplicity of through-holes 2, part of which is of an essentially circular configuration. The balance of the through-holes is constructed as elongate holes (cf. FIG. 1 and FIG. 2). The entire bristle carrier 1 is manufactured as a plastic injection-molded part. The through-holes 2 can be formed simultaneously with the injection-molding operation.

Figure 4:
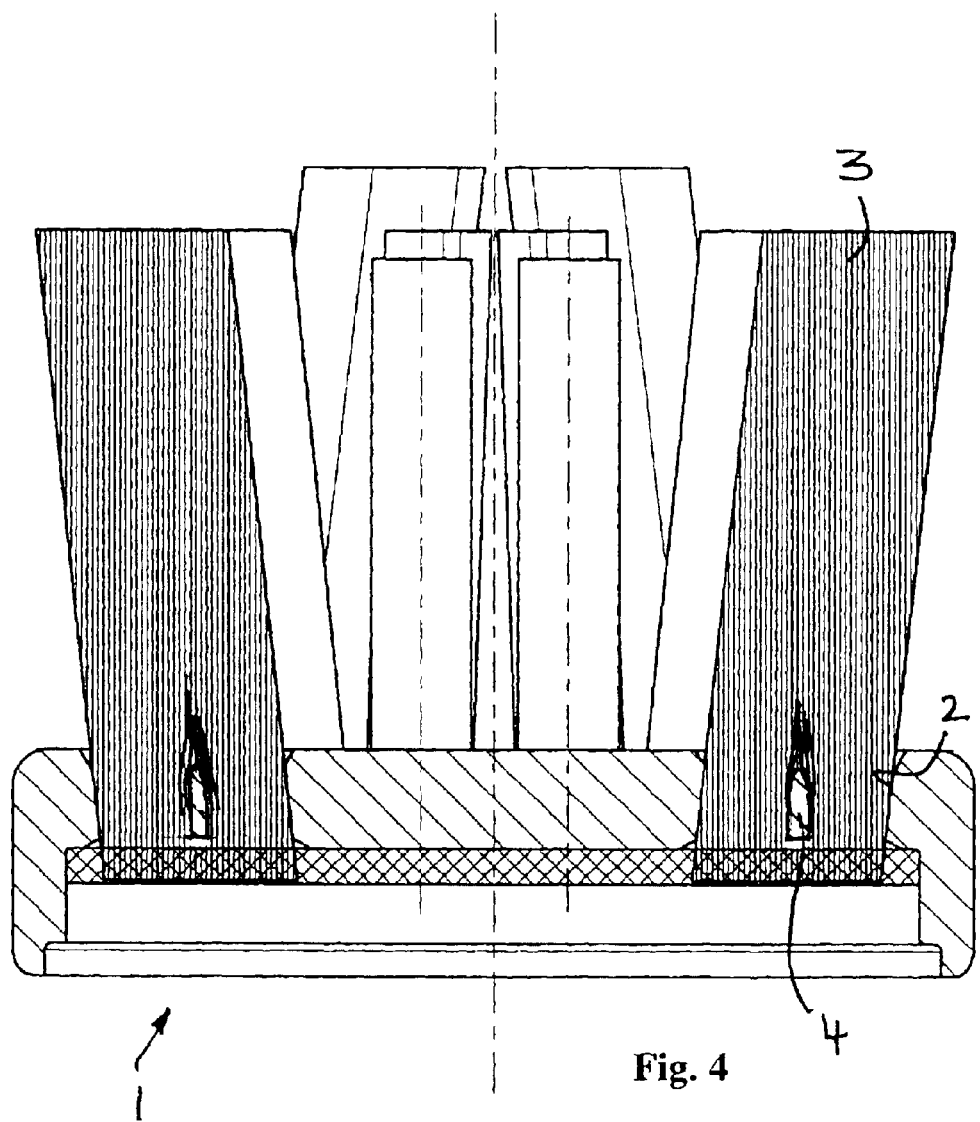
FIG. 4 is a sectional view of the bristle carrier of FIG. 1 taken along the line 5—5 of FIG. 1, showing the tufts in an inserted condition.

As is shown in FIG. 4, a multiplicity of bristles is arranged in the holes 2 in the bristle carrier 1 so that they are seated in the holes 2 in the form of tufts 3. Each hole 2 receives one tuft 3 which, as FIG. 4 shows, can be arranged at different angles of tilt. The tufts 3 also have different outer contours. The tufts 3 seated in the elongate holes 2 likewise have an elongated and closed outer contour which can essentially correspond to the elongate contour of the associated hole 2. The tufts 3 seated in the circular holes 2 form conventional tufts that are likewise constructed with a circular cross section.

As FIG. 4 shows, the tufts 3 are fastened without anchors in the holes 2. With a first end they pass through the through-holes 2 and project out from the rear side of the bristle carrier 1. The ends projecting from the rear side of the bristle carrier 1 are joined together. This can be accomplished, for example, by means of a hot embossing die which welds together the ends of the bristles at the hole end. It is also possible for the ends of the bristles projecting from the rear side to be fixed in place by means of adhesive. They can also be cast in a molded element made of a different material, in particular a thermoplastic, so that the ends of the bristles at the hole end are securely fixed in place. As FIG. 4 shows, the bristles from different tufts can also be welded together, with the result that the bristles are fixedly located in an on the whole plate-shaped configuration on the rear side of the bristle carrier 1.

As FIG. 1 shows, the elongate holes 2 are each divided by one transverse wall 4 into two segments. The transverse wall 4 is integrally molded to the bristle carrier 1, preferably being cast to it during the injection molding. Each transverse wall 4 extends in a direction transverse to the longitudinal axis of the elongate hole 2, linking the hole's opposing longitudinal sides (cf. FIG. 1). The integral construction of the transverse walls 4 can be seen particularly well in FIG. 3.

The resulting segments of the elongate through-holes 2 are bounded by opposing longitudinal walls of the holes 2, one of the arcuately curved end walls of the elongate holes 2, and finally by one side of the transverse wall 4. Hence on the whole they have a semi-oval contour. The transverse wall 4 divides the respective holes 2 in the middle, thus resulting in hole segments of equal size. It will be understood, of course, that, depending on their size or geometry, the holes 2 can also have several transverse walls 4.

Figure 5:
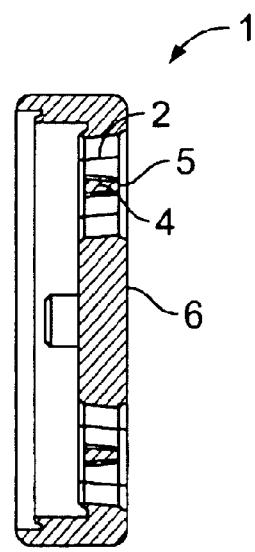
FIG. 5 is a sectional view of the bristle carrier without bristles taken along the line 5—5 of FIG. 1.
Figures 6, 6A:
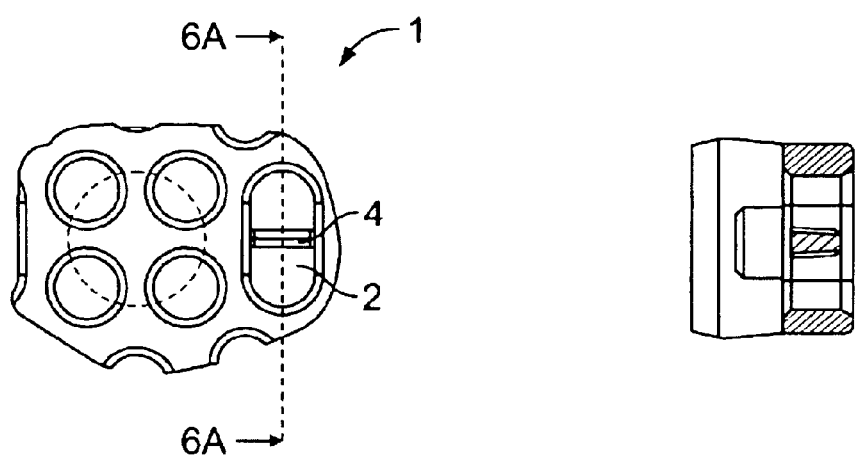
FIG. 6 is a detail view of Area 6 in FIG. 1.
FIG. 6A is a sectional view taken along line 6A–6A of FIG. 6.
Figure 7:
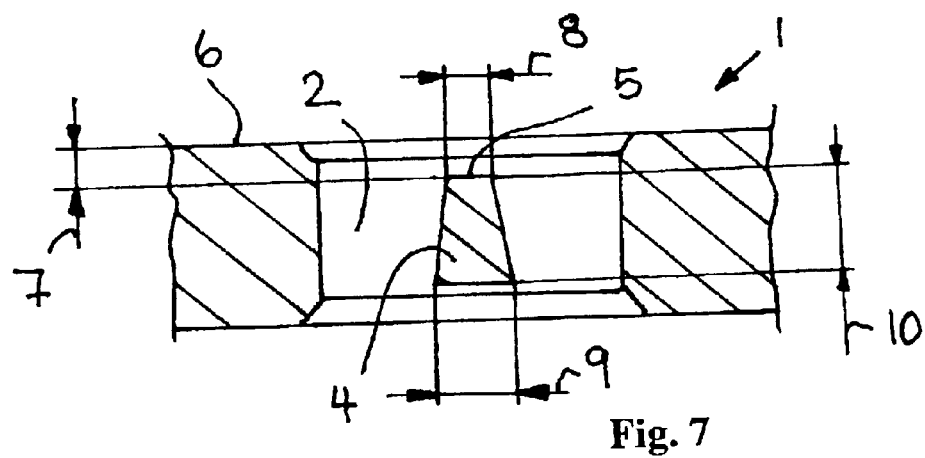
FIG. 7 is a detail view, in section, in accordance with a further preferred embodiment of the invention.

As is shown in particular in FIGS. 5 and 6, the transverse walls 4 are recessed within the holes 2, meaning that an upper edge 5 of the transverse walls 4 lies deeper than the upper side 6 of the bristle carrier 1 bordering on the holes 2. As FIG. 7 shows, the difference in height 7 between the upper edge 5 of the transverse wall and the upper side 6 of the bristle carrier 1 amounts to just a fraction of a millimeter. According to a preferred embodiment of the invention the upper edge 5 can be recessed by approximately 0.1 mm to 0.5 mm, in particular around 0.3 mm, relative to the upper side 6 of the bristle carrier.

The lower edge of the transverse wall 4 can also be recessed a little into the hole 2 in relation to the lower side of the bristle carrier 1. In this case, too, the amount by which the transverse wall 4 is shortened can amount likewise to a fraction of a millimeter.

To prevent the respective tuft 3 from fanning out due to the transverse wall 4 it is possible for the transverse wall 4 to taper in thickness toward the upper side 6 of the bristle carrier 1 (cf. FIG. 6 and FIG. 7). The conicity toward the upper side can be varied in degree. The thickness of the transverse wall 4 in the area of its upper edge 5 can amount to between 0.2 and 0.7 times the thickness of the transverse wall. In the embodiment shown in FIG. 7 the thickness 8 at the upper edge 5 can amount to around 0.25 mm, while the thickness 9 at the lower edge of the transverse wall 4 can amount to around 0.5 mm. The average thickness of the transverse wall 4 thus lies on the whole within the range of a fraction of a millimeter. It preferably amounts to between 0.25 mm and 0.5 mm. The height 10 of the transverse wall 4 is adapted to the thickness of the bristle carrier 1. It is preferably a little less than the thickness of the bristle carrier 1. According to a preferred embodiment as shown in FIG. 7 the height 10 of the transverse wall 4 can amount to around 0.3 mm to 0.7 mm, preferably around 0.5 mm. The corresponding angle of conicity results accordingly. In addition to its function of preventing gaps in the respective tuft, the conical construction of the transverse wall 4 also makes it easier to insert the bristles from the upper side 6 of the bristle carrier 1 into the hole 2.

For an improved smooth merging of the bristles, which are arranged in the various segments, into a joint, dense tuft it is possible for the upper edge 5 of the transverse wall 4 to be of a rounded configuration (cf. FIG. 6). This improves the insertion of the bristles and reduces the load exerted on the bristles by the upper edge of the transverse wall 4 when the bristles are accordingly bent. Suitable bevels can be provided at the opening of the holes 2 toward the upper side 6 of the bristle carrier 1.

As FIG. 4 shows, different tufts are conveniently arranged at different angles of tilt, meaning that not all the tufts 3 project from the bristle carrier 1 perpendicular to its upper side 6. To arrange the tufts 3 at suitable angles of tilt the walls of the respective holes 2 are correspondingly inclined. As FIG. 5 shows, the elongate holes 2 can have inclined end walls which run parallel to each other and are inclined relative to the upper side normal of the bristle carrier 1 at an acute angle that can have values of up to around 30°.

The transverse walls 4 dividing the respective hole 2 can also be arranged a various angles of inclination corresponding to the different angles of tilt of the respective tufts 3. In the case of tufts that project out in a straight-line configuration, as shown in FIG. 6, it can be an advantage to arrange the transverse wall 4 likewise perpendicular to the upper side 6 of the bristle carrier 1.

In the case of tilted tufts as shown in FIG. 5, the transverse walls 4 can likewise be constructed at an inclination. According to FIG. 5 they are inclined parallel to the end walls of the elongate holes 2. In this case they extend parallel to the longitudinal axis of the tufts 3 and can be inclined at an angle of up to 30°.

Figure 8:
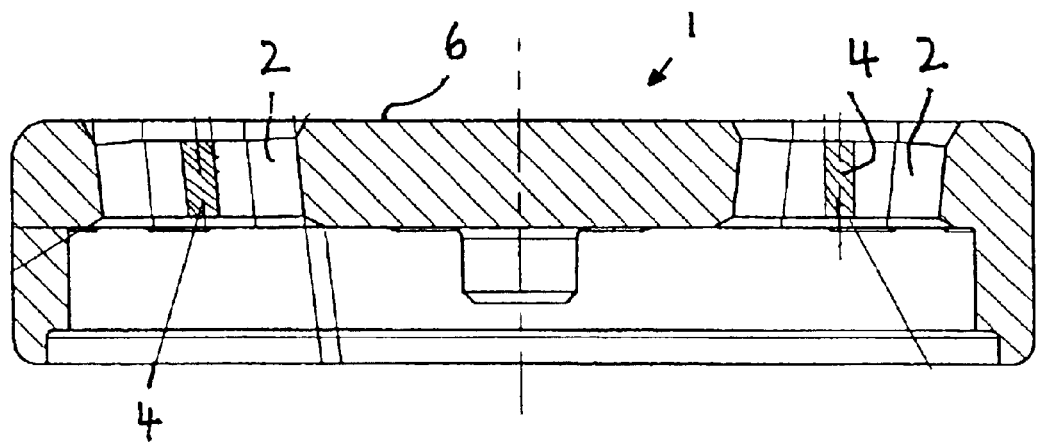
FIG. 8 is a sectional view of a bristle carrier similar to FIG. 5, showing different embodiments of the invention in which the transverse walls arranged in the holes are arranged at different angles of inclination.

The arrangement of the transverse walls 4 parallel to the longitudinal axis of the tufts 3 is not compulsory, however. With an inclined construction of the walls of the hole 2 it is possible, however, for the transverse wall 4 to be arranged perpendicular to the upper side 6 of the bristle carrier 1 in order, for example, to facilitate removal from an injection mold. Such an embodiment of the invention can be seen on the right-hand side of FIG. 8.

Furthermore, provision can be made for the transverse walls 4 to be arranged neither perpendicular to the upper side 6 nor parallel to the inclination of the hole walls. According to a further embodiment of the invention, which is not separately shown, provision can be made for the walls of the hole 2 to be inclined to one side and for the transverse wall dividing the corresponding hole to be inclined toward the other side.

The transverse walls 4 act in the elongate holes 4 as support walls. They support the bristles in particular when bending in the direction of the longitudinal axis of the holes. The effective free bending length of the bristles, which are fastened only at their ends, is shortened and their deflection is restricted already within the holes. It is thus possible to obtain a higher stiffness of the tufts or the perception of a harder bending characteristic of the tufts. This supports the cleaning action in advantageous manner. The restricted bending and movement of the bristles can prolong the service life, reducing premature wear.

On the other hand, if the transverse walls are also used in the method referred to as anchor-free tufting, the seating of the tufts 3 in the holes largely approximates to that of the anchor tufting method, thus enabling corresponding characteristics to be achieved or transferred. Hence it is possible to use comparable production parameters in spite of the different anchoring of the bristles, and the results of clinical tests are transferable. This results in a considerable reduction of cost and development effort.

What is claimed is:

1. A toothbrush head, comprising
   a bristle carrier sized for insertion into a human mouth, and
   bristles constructed to brush teeth attached to said bristle carrier, said bristles being grouped in tufts that are seated in multiple holes in the bristle carrier and fastened by their ends close to a rear side of the bristle carrier by one of the group consisting of welded bonds, adhesive bonds and bonds resulting from casting in place,
   at least one hole in the bristle carrier being divided by at least one transverse wall into plural segments, said at least one transverse wall being constructed such that the bristles seated in the segments form a common tuft with a smooth and closed outer contour corresponding to the contour of the hole.

2. The brush head according to claim 1 wherein the hole and the tuft seated therein have an approximately elongated outer contour and at least one transverse wall extends in a direction approximately transverse to a longitudinal axis of the hole, or said hole and the tuft seated therein have a round, angular, oval, circular segmental contour or a combination of such contours.

3. The brush head according to claim 1 wherein the at least one transverse wall has a thickness in the range from 0.2 mm to 0.6 mm, preferably 0.2 to 0.3 mm.

4. The brush head according to claim 1 wherein an upper edge of the at least one transverse wall is recessed relative to an upper side of the bristle carrier.

5. The brush head according to claim 4 wherein a difference in height between the upper edge of the at least one transverse wall and the upper side of the bristle carrier lies in the range from 0.1 mm to 0.7 mm, preferably 0.25 mm to 0.5 mm.

6. The brush head according to claim 1 wherein the at least one transverse wall tapers in thickness toward its upper edge, being of a conical configuration.

7. The brush head according to claim 1 wherein an upper edge of the transverse wall is rounded off.

8. The brush head according to claim 1 wherein the at least one transverse wall is integrally constructed in one piece with the bristle carrier.

9. The brush head according to claim 1 wherein the transverse wall is constructed as a part separate from the bristle carrier and subsequently inserted in the hole.

10. The brush head according to claim 1 wherein the at least one hole is divided into segments of roughly the same size.

11. The brush head according to claim 1 wherein the holes are through-holes and the bristle carrier is of an essentially plate-shaped configuration.

12. The brush head according to claim 1 wherein different bristles are seated in different segments of the at least one hole.

13. The brush head according to claim 1 wherein the segments have a non-circular contour, in particular a polygonal contour with at least two roughly parallel sides.

14. The brush head according to claim 1 wherein the at least one transverse wall is arranged perpendicular to an upper side of the bristle carrier.

15. The brush head according to claim 1 wherein the at least one transverse wall is arranged at an acute angle to a bristle carrier normal standing perpendicular to a bristle carrier upper side.

16. The brush head according to claim 15 wherein the transverse wall is inclined relative to the bristle carrier normal at an angle corresponding approximately to an angle of inclination of an end wall of the hole relative to said bristle carrier normal.

17. A method of making a toothbrush head, comprising
    providing a bristle carrier having multiple holes and sized for insertion into a human mouth,
    dividing at least one said hole by at least one transverse wall into plural segments, and attaching bristles constructed to brush teeth and grouped in tufts in said holes in said bristle carrier by fastening ends of said bristles close to a rear side of the bristle carrier by one of the group consisting of welded bonds, adhesive bonds and bonds resulting from casting in place, said at least one transverse wall being constructed such that the bristles seated in the segments form a common tuft with a smooth and closed outer contour corresponding to the contour of the hole.

18. The method of claim 17 wherein said dividing includes integrally constructing said transverse wall and said bristle carrier in one piece.

19. The method of claim 18 wherein said bristle carrier is injection-molded of plastic together with the transverse wall.

20. The method of claim 17 wherein the at least one transverse wall has a thickness in the range from 0.2 mm to 0.6 mm, preferably 0.2 to 0.3 mm.

21. The method of claim 17 wherein an upper edge of the at least one transverse wall is recessed relative to an upper side of the bristle carrier.

22. The method of claim 21 wherein a difference in height between the upper edge of the at least one transverse wall and the upper side of the bristle carrier lies in the range from 0.1 mm to 0.7 mm, preferably 0.25 mm to 0.5 mm.

23. The method of claim 17 wherein the at least one transverse wall tapers in thickness toward its upper edge, being of a conical configuration.

24. The method of claim 17 wherein an upper edge of the transverse wall is rounded off.

25. The method of claim 17 wherein the segments have a non-circular contour, in particular a polygonal contour with at least two roughly parallel sides.

26. The method of claim 17 wherein the at least one transverse wall is arranged perpendicular to an upper side of the bristle carrier.

27. The method of claim 17 wherein the holes are through-holes.

* * * * *